(12) United States Patent
Kroll

(10) Patent No.: US 7,212,859 B1
(45) Date of Patent: May 1, 2007

(54) DUAL-CHAMBER IMPLANTABLE CARDIAC STIMULATION SYSTEM AND DEVICE WITH SELECTABLE ARRHYTHMIA TERMINATION ELECTRODE CONFIGURATIONS AND METHOD

(75) Inventor: Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 701 days.

(21) Appl. No.: 10/206,460

(22) Filed: Jul. 26, 2002

Related U.S. Application Data

(63) Continuation of application No. 09/514,737, filed on Feb. 28, 2000, now Pat. No. 6,456,876.

(51) Int. Cl.
*A61N 1/368* (2006.01)
(52) U.S. Cl. .......................................... 607/14; 607/63
(58) Field of Classification Search ................ 607/4, 607/5, 63, 14
See application file for complete search history.

(56) References Cited

U.S. PATENT DOCUMENTS

| | | | | |
|---|---|---|---|---|
| 4,712,555 | A | 12/1987 | Thornander et al. ........ | 128/419 |
| 4,788,980 | A | 12/1988 | Mann et al. ................ | 128/419 |
| 4,940,052 | A | 7/1990 | Mann et al. ................ | 128/419 |
| 4,944,298 | A | 7/1990 | Sholder ........................ | 128/419 |
| 5,163,427 | A * | 11/1992 | Keimel ........................... | 607/5 |
| 5,165,403 | A * | 11/1992 | Mehra ......................... | 607/122 |
| 5,209,229 | A | 5/1993 | Gilli ............................ | 128/419 |
| 5,314,430 | A | 5/1994 | Bardy ............................ | 607/5 |
| 5,411,528 | A | 5/1995 | Miller et al. ................... | 607/5 |
| 5,441,518 | A | 8/1995 | Adams et al. ................. | 607/5 |
| 5,531,764 | A | 7/1996 | Adams et al. ................. | 607/5 |
| 5,549,642 | A * | 8/1996 | Min et al. ...................... | 607/5 |
| 5,641,326 | A | 6/1997 | Adams .......................... | 607/5 |
| 5,690,686 | A | 11/1997 | Min et al. ...................... | 607/5 |
| 5,713,926 | A | 2/1998 | Hauser et al. ................. | 607/5 |
| 5,766,226 | A * | 6/1998 | Pedersen ........................ | 607/5 |
| 5,830,236 | A | 11/1998 | Mouchawar et al. .......... | 607/5 |
| 5,906,633 | A | 5/1999 | Mouchawar et al. .......... | 607/5 |
| 5,978,704 | A | 11/1999 | Ideker et al. .................. | 607/5 |
| 5,987,354 | A * | 11/1999 | Cooper et al. ................. | 607/5 |
| 6,067,471 | A * | 5/2000 | Warren .......................... | 607/5 |
| 6,091,989 | A * | 7/2000 | Swerdlow et al. ............. | 607/5 |
| 6,647,291 | B1* | 11/2003 | Bonner et al. ................. | 607/5 |

FOREIGN PATENT DOCUMENTS

EP 0 813 889 A2 12/1997
WO WO 00/04950 2/2000

* cited by examiner

*Primary Examiner*—Kennedy Schaetzle

(57) ABSTRACT

An implantable cardiac stimulation system delivers arrhythmia termination pulses to the ventricles and the atria of a heart. The system includes an implantable cardiac stimulation device, including a conductive enclosure, ventricular arrhythmia termination pulse generator, and an atrial arrhythmia termination pulse generator. A first electrode configuration, including the conductive enclosure, is arranged to be coupled to the ventricular pulse generator to terminate ventricular arrhythmias and a second electrode configuration, electrically independent from the conductive enclosure and confined within the heart, is arranged to be coupled to the atrial pulse generator to terminate atrial arrhythmias.

17 Claims, 2 Drawing Sheets

DUAL-CHAMBER IMPLANTABLE CARDIAC STIMULATION SYSTEM AND DEVICE WITH SELECTABLE ARRHYTHMIA TERMINATION ELECTRODE CONFIGURATIONS AND METHOD

CROSS-REFERENCE TO RELATED APPLICATIONS

This application is a continuation of U.S. patent application Ser. No. 09/514,737, filed Feb. 28, 2000, now issued as U.S. Pat. No. 6,456,876.

FIELD OF THE INVENTION

The present invention is generally directed to a dual-chamber implantable cardiac defibrillator (ICD), system and method. The present invention is more particularly directed to a dual-chamber ICD, system and method wherein electrode configurations for ventricular arrhythmia termination and atrial arrhythmia termination are selectable from among a plurality of electrode configurations.

BACKGROUND OF THE INVENTION

Implantable cardiac defibrillators (ICDs) are well known in the art. These devices, encapsulated in a conductive housing or enclosure, are generally implanted in the left pectoral region of a patient and electrically connected to the heart with one or more electrode-carrying leads. One lead includes at least one defibrillation electrode arranged to be positioned in the right ventricle. An arrhythmia detector detects ventricular arrhythmias, such as ventricular fibrillation. When such an arrhythmia is detected, a pulse generator delivers a defibrillating shock from the defibrillation electrode in the right ventricle to the conductive housing to terminate the arrhythmia. Alternatively, such arrhythmia terminating systems may further include another defibrillation electrode positioned in the right atrium and electrically connected to the conductive housing. In this arrangement, the defibrillating shock is delivered from the parallel connected right atrial electrode and the conductive housing to the right ventricular electrode.

Implantable atrial defibrillators are also known. These devices are also encapsulated in a conductive housing or enclosure and are electrically coupled to the heart by one or more electrode-carrying leads. The leads are known to include a defibrillation electrode positioned in the right atrium of the heart. When an arrhythmia detector detects an atrial arrhythmia, such as atrial fibrillation, an atrial defibrillating shock is then applied from the right atrial defibrillation electrode to the conductive housing.

Although not presently commercially available, combined implantable dual-chamber (atrial and ventricular) defibrillators continue to be investigated and under development. Because of the vast differences between ventricular and atrial arrhythmias, dual-chamber devices remain a challenge. For example, ventricular fibrillation is an immediately life threatening condition while atrial fibrillation, although uncomfortable and debilitating, is not a life threatening condition. Hence, there must be a preference for effective ventricular fibrillation treatment over atrial fibrillation treatment. Further, unless safety measures are taken in delivering atrial fibrillation terminating shocks, there is a potential for atrial fibrillation terminating shocks inducing ventricular fibrillation. Still further, by the time a ventricular fibrillation terminating shock is delivered, the patients are, in most occurrences, unconscious while, when atrial fibrillation terminating shocks are delivered, the patients are conscious and able to perceive discomfort from the atrial fibrillation termination shocks. Lastly, because of the relative locations of the atria and ventricles, the most effective ventricular fibrillation termination electrode configurations are different from the most effective atrial fibrillation termination electrode configurations.

Hence, in terms of arrhythmia termination, ventricular fibrillation termination electrode configurations must be those which provide the greatest assurance of successful arrhythmia termination. These configurations are those which exhibit the lowest ventricular defibrillation thresholds. In contrast, in arriving at an atrial fibrillation termination electrode configuration, consideration must be given to both atrial termination effectiveness and the degree of perceived discomfort by the patient to the delivered atrial arrhythmia termination shocks. The present invention addresses these issues.

SUMMARY OF THE INVENTION

The present invention provides an implantable cardiac stimulation system, device and method wherein atrial arrhythmia terminating pulses are confined to within the heart while ventricular arrhythmia terminating pulses may be delivered between a defibrillation electrode within the heart and another defibrillation electrode outside of the heart. With this arrangement, effectiveness of ventricular arrhythmia termination may be preserved while atrial arrhythmia termination may be achieved with minimized patient discomfort because the atrial termination pulse currents are confined within the heart and are precluded from recruiting the many pain neurons and skeletal muscle cells of the pectoral region.

In accordance with one embodiment of the present invention, the device and system delivers ventricular arrhythmia terminating pulses with an electrode configuration which includes the conductive housing encapsulating the device and delivers atrial arrhythmia termination pulses with an electrode configuration electrically independent of the conductive housing and thus confined to within the heart.

In accordance with another embodiment, a plurality of atrial arrhythmia terminating electrode configurations are available to the device, wherein each available atrial arrhythmia termination electrode configuration is electrically isolated from the conductive housing and thus confined to within the heart. One of the electrode configurations for atrial arrhythmia termination may be selected for use based upon a common arrhythmia termination characteristic, such as defibrillation energy threshold or perceived discomfort by the patient. The ventricular arrhythmia termination electrode configuration includes an electrode outside of the heart, such as the conductive device housing, to maintain ventricular arrhythmia termination effectiveness.

In accordance with a further aspect of the present invention, a preferred embodiment delivers a rounded, reduced-pain waveform for the atrial therapy as described in U.S. Pat. Nos. 5,906,633 and 5,830,236 which are incorporated herein by reference.

In accordance with a still further aspect of the present invention, a first plurality of electrode configurations are provided for ventricular arrhythmia termination, wherein at least one of the first plurality of electrode configurations includes the conductive device housing, and a second plurality of electrode configurations are provided for atrial arrhythmia termination, wherein each of the second plurality of electrode configurations is electrically isolated from the conductive device housing. A first electrode configuration from among the first plurality of electrode configurations may be selected for use based upon a common arrhythmia terminating characteristic, such as arrhythmia termination energy threshold. A second electrode configuration from among the second plurality of electrode configurations may be selected for use based upon a common arrhythmia termination characteristic such as arrhythmia termination energy threshold or perceived discomfort by the patient to the atrial arrhythmia termination pulses.

The cardiac stimulation device includes an electrode configuration selector, such as a switch, which selectively couples an atrial arrhythmia pulse generator to a pair of terminals which are coupled to the selected atrial arrhythmia termination electrode configuration and which selectively couples a ventricular arrhythmia termination pulse generator to a pair of terminals coupled to the selected ventricular arrhythmia termination electrode configuration.

As a result, by virtue of the present invention, ventricular arrhythmia termination effectiveness may be maintained while permitting flexibility in the selection of an atrial arrhythmia termination electrode configuration to achieve effective atrial arrhythmia termination with a minimum of perceived discomfort by the patient.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
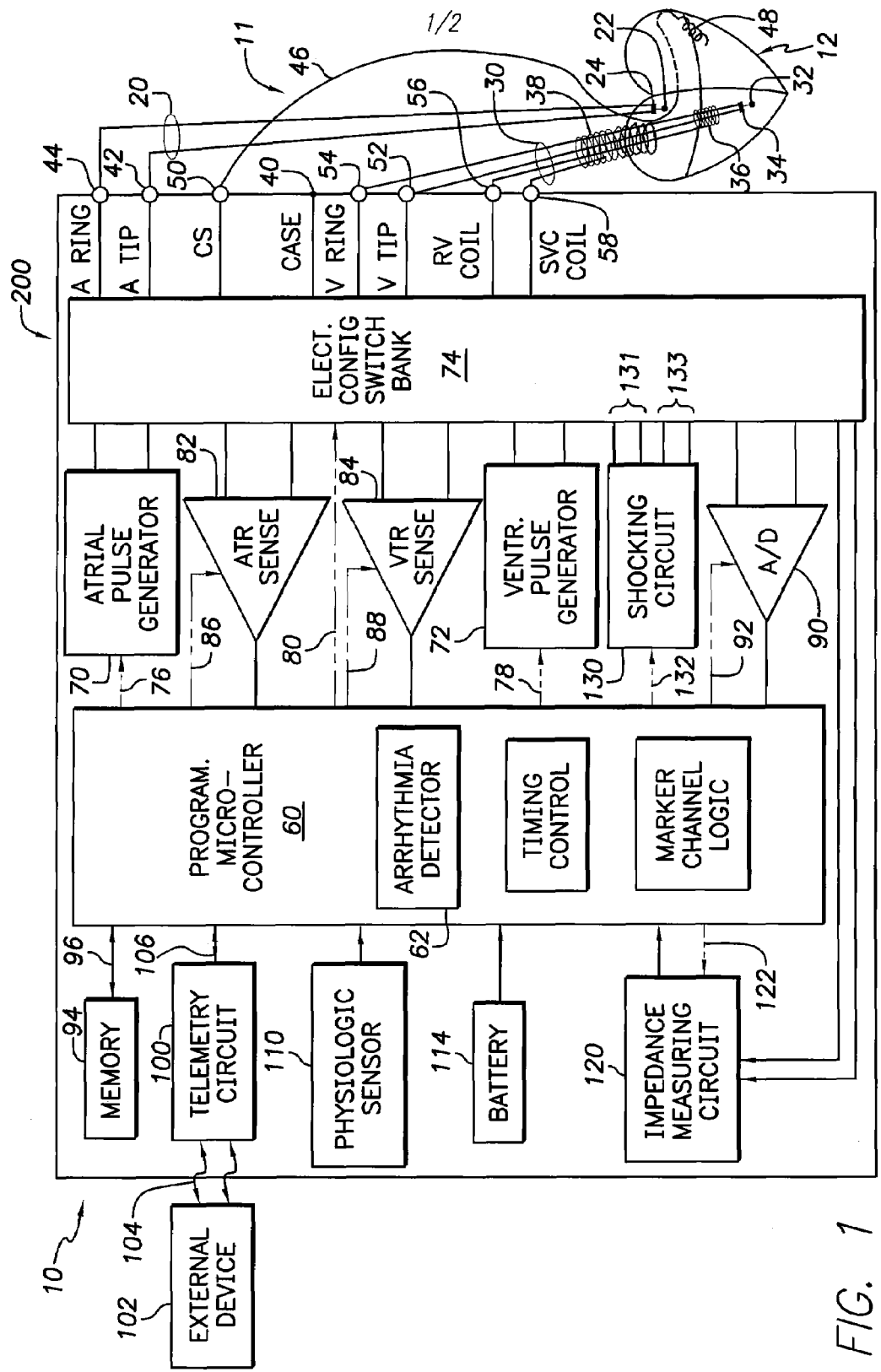
FIG. 1 is a functional block diagram of a dual-chamber implantable stimulation device illustrating the basic elements of a stimulation device which can provide cardioversion, defibrillation and pacing stimulation.

In FIG. 1, a simplified block diagram is shown of an implantable cardiac stimulation system 200 including a dual-chamber implantable stimulation device 10 and a lead system 11. The system 200, as will be seen hereinafter, is capable of treating both fast and slow arrhythmias with stimulation therapy, including atrial and ventricular cardioversion, defibrillation, and pacing stimulation. While a combined pacer and defibrillator device is shown, this is for illustration purposes only, and one of skill in the art could readily eliminate or disable the pacing circuitry to provide a single or dual-chamber defibrillation device or add circuitry to provide a device capable of providing stimulation or defibrillation to three or four cardiac chambers without departing from the present invention.

To provide atrial chamber pacing stimulation and sensing, the implantable stimulation device 10 is shown in electrical communication with a patient's heart 12 by way of an implantable atrial lead 20 of lead system 11 having an atrial tip electrode 22 and an atrial ring electrode 24 which typically is implanted in the patient's atrial appendage.

The implantable stimulation device 10 is also shown in electrical communication with the patient's heart 12 by way of an implantable ventricular lead 30 of lead system 11 having, in this embodiment, a ventricular tip electrode 32, a ventricular ring electrode 34, a right ventricular (RV) coil defibrillation electrode 36, and a coil defibrillation electrode 38. Typically, the ventricular lead 30 is transvenously inserted into the heart 12 so as to place the RV coil electrode 36 in the right ventricular apex, and the coil electrode 38 in the superior vena cava or the right atrium. Accordingly, the ventricular lead 30 is capable of receiving cardiac signals and delivering stimulation in the form of pacing and shock therapy to the right ventricle and right atrium.

Further, in accordance with this preferred embodiment, the lead system preferably includes a coronary sinus (CS) lead 46 having a coil defibrillation electrode 48. The CS lead 46 may be advanced through the SVC, into the right atrium, through the os or ostium of the coronary sinus, and into the coronary sinus for placing the electrode 48 adjacent the left atrium and the left ventricle. Alternatively, the lead 46 may be advanced into any of the left ventricular veins, such as the left cardiac vein. Although not illustrated in FIG. 1, the lead 46 may further include a distal pacing electrode to provide pacing stimulation to the left side of the heart along with atrial and ventricular cardioversion and/or defibrillation by electrode 48. For example, a lead designed for placement in the coronary sinus region could be implanted to deliver left atrial pacing, atrial shocking therapy, left ventricular pacing and left ventricular shocking stimulation.

The housing 40 (shown schematically) for the implantable stimulation device 10 includes a connector (not shown) having an atrial tip terminal 42 and an atrial ring terminal 44, which are adapted for connection to the atrial tip electrode 22 and the atrial ring electrode 24, respectively. The housing 40 further includes a ventricular tip terminal 52, a ventricular ring terminal 54, a ventricular shocking terminal 56, and an SVC shocking terminal 58, which are adapted for connection to the ventricular tip electrode 32, the ventricular ring electrode 34, the RV coil electrode 36, and the SVC coil electrode 38, respectively. The housing 40 still further includes a CS pin terminal 50 adapted for connection to the CS coil electrode 48. The housing 40 (often referred to as the "enclosure", "can", "case" or "case electrode") encapsulates the circuitry of the implantable stimulation device 10 and is formed of electrically conductive material. It may be programmably selected to serve as a return defibrillation electrode, alone or in combination with one of the coil electrodes.

In accordance with the present invention, the case 40 and coil defibrillation electrodes 36, 38, and 48 provide a plurality of selectable ventricular arrhythmia termination electrode configurations and a plurality of atrial arrhythmia termination electrode configurations. Further, in accordance with the present invention, at least one ventricular arrhythmia termination electrode configuration employs the case 40, which has proven to provide effective ventricular arrhythmia termination, and each one of the atrial arrhythmia termination electrode configurations is electrically isolated or independent of the case 40 to confine the atrial arrhythmia termination shock currents to within the heart to minimize the perception of discomfort by the patient to the atrial arrhythmia terminating shocks.

For example, in accordance with this embodiment, the ventricular arrhythmia termination electrode configurations may include the case 40 as a cathode and the RV coil electrode 36 as an anode. Another electrode configuration may include the CS coil electrode 48 as a cathode and the RV coil electrode 36 as an anode. Lastly, another configuration may include the RA coil electrode 38 and the CS coil electrode 48 coupled together as a cathode and the RV coil electrode 36 as an anode.

With respect to atrial arrhythmia termination, the electrode configurations may include the CS coil electrode 48 as an anode and the RA coil electrode 38 as a cathode. Another configuration may include the RV coil electrode 36 as an anode and the RA coil electrode 38 as a cathode. Lastly, the CS coil electrode 48 and RV coil electrode 36 may be connected together as an anode and the RA coil electrode 48 employed as a cathode. Each one of the above atrial arrhythmia termination electrode configurations is electrically independent or isolated from the case 40 and confined within the heart 12.

At the core of the implantable stimulation device 10 is a programmable microcontroller 60 which controls the various modes of stimulation therapy. As is well known in the art, the microcontroller 60 includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions is well known in the art. Representative types of control circuitry that may be used with the invention include the microprocessor-based control system of U.S. Pat. No. 4,940,052 (Mann et al.) and the state-machines of U.S. Pat. No. 4,712,555 (Thornander et al.) and U.S. Pat. No. 4,944,298 (Sholder). For a more detailed description of the various timing intervals used within the stimulation device and their inter-relationship, see U.S. Pat. No. 4,788,980 (Mann et al.). The '052, '555, '298 and '980 patents are incorporated herein by reference.

As shown in FIG. 1, an atrial pulse generator 70 and a ventricular pulse generator 72 generate pacing stimulation pulses for delivery by the atrial lead 20 and the ventricular lead 30, respectively, via a switch bank 74. The pulse generators, 70 and 72, are controlled by the microcontroller 60 via appropriate control signals, 76 and 78, respectively, to trigger or inhibit the stimulation pulses. The microcontroller 60 further includes timing circuitry that controls the timing of such stimulation pulses (e.g., pacing rate and atrio-ventricular (AV) delay), as well as keeping track of the timing of any refractory periods, PVARP intervals, noise detection windows, evoked response windows, alert intervals, marker channel timing, etc., that are well known in the art.

The switch bank 74 includes a plurality of switches for switchably connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar or bipolar) by selectively closing the appropriate combination of switches as is known in the art.

An atrial sense amplifier 82 and a ventricular sense amplifier 84 are also coupled to the atrial and ventricular leads 20 and 30, respectively, through the switch bank 74 for detecting the presence of cardiac activity. The switch bank 74 determines the "sensing polarity" of the cardiac signal by selectively closing the appropriate switches, as is also known in the art. In this way, the clinician may program the sensing polarity independent of the stimulation polarity.

Each sense amplifier, 82 and 84, preferably employs a low power, precision amplifier with programmable gain and/or automatic gain control, bandpass filtering, and a threshold detection circuit, known in the art, to selectively sense the cardiac signal of interest. The automatic gain control enables the implantable stimulation device 10 to deal effectively with sensing the low frequency, low amplitude signal characteristics of atrial and ventricular fibrillation.

The outputs of the atrial and ventricular sense amplifiers, 82 and 84, are connected to the microcontroller 60 which, in turn, inhibits the atrial and ventricular pulse generators, 70 and 72, respectively, in a demand fashion whenever cardiac activity is sensed in the respective chambers. The sense amplifiers, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sense amplifiers, 82 and 84, as is known in the art.

For arrhythmia detection, the device includes an arrhythmia detector 62 which utilizes the atrial and ventricular sense amplifiers, 82 and 84, to sense cardiac signals to determine whether a rhythm is physiologic or pathologic. As used herein, "sensing" is reserved for the noting of an electrical depolarization, and "detection" is the processing of these sensed depolarization signals and noting the presence of an arrhythmia. The timing intervals between sensed events (e.g., the P—P and R—R intervals) are then classified by the microcontroller 60 by comparing them to a predefined rate zone limit (i.e., bradycardia, normal, low rate VT, high rate VT, and atrial and ventricular fibrillation rate zones) and various other characteristics (e.g., sudden onset, stability, physiologic sensors, and morphology, etc.) in order to determine the type of arrhythmia detected (e.g., bradycardia, tachycardia, and atrial or ventricular fibrillation), to employ a corresponding arrhythmia terminating therapy, also known as "tiered therapy").

Cardiac signals are also applied to the inputs of an analog to digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the atrial and ventricular leads, 20 and 30, through the switch bank 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the implantable stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable stimulation device 10 may be non-invasively programmed into the memory 94 through a telemetry circuit 100 in telemetric communication with an external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the implantable stimulation device 10 (as contained in the microcontroller 60 or memory 94) to be sent to the external device 102 through an established communication link 104.

In the preferred embodiment, the implantable stimulation device 10 further includes a physiologic sensor 110. Such sensors are commonly called "rate-responsive" sensors. The physiological sensor 110 is used to detect the exercise state of the patient, to which the microcontroller 60 responds by adjusting the rate and AV Delay at which the atrial and ventricular pulse generators, 70 and 72, generate stimulation pulses. The type of sensor used is not critical to the present invention and is shown only for completeness.

The stimulation device additionally includes a battery 114 which provides operating power to all of the circuits shown in FIG. 1. For the implantable stimulation device 10, which employs shocking therapy, the battery 114 must be capable of operating at low current drains for long periods of time (preferably less than 10 µA), and then be capable of providing high-current pulses (for capacitor charging) when the patient requires a shock pulse (preferably, in excess of 2 A, at voltages above 2 V, for periods of 10 seconds or more). The battery 114 preferably has a predictable discharge characteristic so that elective replacement time can be detected. Accordingly, the implantable stimulation device 10 preferably employs lithium/silver vanadium oxide batteries, as is true for most (if not all) current devices.

The implantable stimulation device 10 further includes a magnet detection circuitry (not shown), coupled to the microcontroller 60. It is the purpose of the magnet detection circuitry to detect when a magnet is placed over the implantable stimulation device 10, which magnet may be used by a clinician to perform various test functions of the implantable stimulation device 10, such as defibrillation threshold tests, and/or to signal the microcontroller 60 that an external programmer 102 is in place to receive or transmit data to the microcontroller 60 through the telemetry circuits 100.

It is the primary function of the implantable stimulation device 10 to function as an implantable dual-chamber cardioverter/defibrillator (ICD) device. That is, it must detect the occurrence of an atrial or ventricular arrhythmia, such as atrial fibrillation or ventricular fibrillation, and automatically apply an appropriate electrical shock therapy to the heart 12 with an appropriate electrode configuration for terminating the detected arrhythmia. To this end, the microcontroller 60 further controls a shocking circuit 130. The shocking circuit 130 has a first pair of outputs 131 for delivering ventricular arrhythmia (such as ventricular fibrillation) terminating pulses and a second pair of outputs 133 for delivering atrial arrhythmia (such as atrial fibrillation) terminating pulses. The magnitude of the pulse energies and the outputs to be used (atrial or ventricular) are controlled by a control signal 132.

To that end, the shocking circuit 130 is capable of generating shocking pulses of low (up to 0.5 joules), moderate (0.5–10 joules), or high energy (11–40 joules), as controlled by the microcontroller 60. Such shocking pulses are applied to the patient's heart through an electrode configuration from among the plurality of electrode configurations previously described and selected by the microcontroller 60. For example, the microcontroller may select the RV and case (electrodes, 36 and 40) for ventricular defibrillation and the RA and CS (electrodes, 38 and 48) for atrial defibrillation. The selection by the microcontroller 60 is implemented by the switch bank 74 for connecting the appropriate output pair, 131 or 133, to the appropriate device terminals (50, 40, 56, 58).

Ventricular cardioversion and atrial defibrillation shocks are generally considered to be of low to moderate energy level (so as to minimize pain felt by the patient), and/or synchronized with an R-wave and/or pertaining to the treatment of atrial fibrillation or ventricular tachycardia. Ventricular defibrillation shocks are generally of moderate to high energy level (i.e., corresponding to thresholds in the range of 5–40 joules), delivered asynchronously (since R-waves may be too disorganized), and pertaining exclusively to the treatment of ventricular fibrillation. Accordingly, the microcontroller 60 is capable of controlling the energy magnitude of and the electrode configuration used to apply the shocking pulses. Preferably, the device has the option of delivering a rounded, reduced-pain waveform for the atrial therapy as described in U.S. Pat. Nos. 5,906,633 and 5,830,236 which are incorporated herein by reference.

The electrode configurations from among the plurality of electrode configurations for atrial and ventricular defibrillation may be preprogrammed by the physician. The selection of the particular electrode configuration to be used may be based upon a common arrhythmia terminating characteristic. The evaluation may be performed by the physician, using the magnet and external device as previously described, or it may be performed by the device itself. For example, for ventricular defibrillation, the electrode configuration selection may be based upon a ventricular defibrillation threshold. In this case, the minimum energy required to defibrillate the ventricles is determined for each available ventricular defibrillation electrode configuration and the one exhibiting the lowest energy threshold is selected. Similarly, for atrial defibrillation, the common arrhythmia terminating characteristic may be based upon an atrial defibrillation threshold and/or the degree of perceived pain by the patient. Each available atrial defibrillation electrode configuration is evaluated with respect to these characteristics. The electrode configuration yielding the lowest values for these characteristics may then be selected. It is possible, however, that the electrode configuration yielding the lowest perceived pain is not the one which yields the lowest defibrillation threshold. In this case, the physician must make a choice having in mind the pain tolerance of the patient.

Once the evaluations are made, the selected electrode configurations are stored in memory 94. Thereafter, a first electrode configuration, from among the plurality of ventricular defibrillation electrode configurations, will be selected by the microcontroller 60 and switch bank 74 for delivering ventricular defibrillation pulses from the shocking circuit 130 at outputs 131 to the heart 12 when ventricular fibrillation is detected. Similarly, a second electrode configuration, from among the plurality of atrial defibrillation electrode configurations, will be selected by the microcontroller 60 and switch bank 74 for delivering atrial defibrillation pulses from the shocking circuit 130 at outputs 133 to the heart 12 when atrial fibrillation is detected.

Because there are many electrode configurations available for ventricular and atrial fibrillation, ventricular defibrillation effectiveness will be assured while permitting effective atrial fibrillation with a low perception of pain on the part of the patient.

Figure 2:
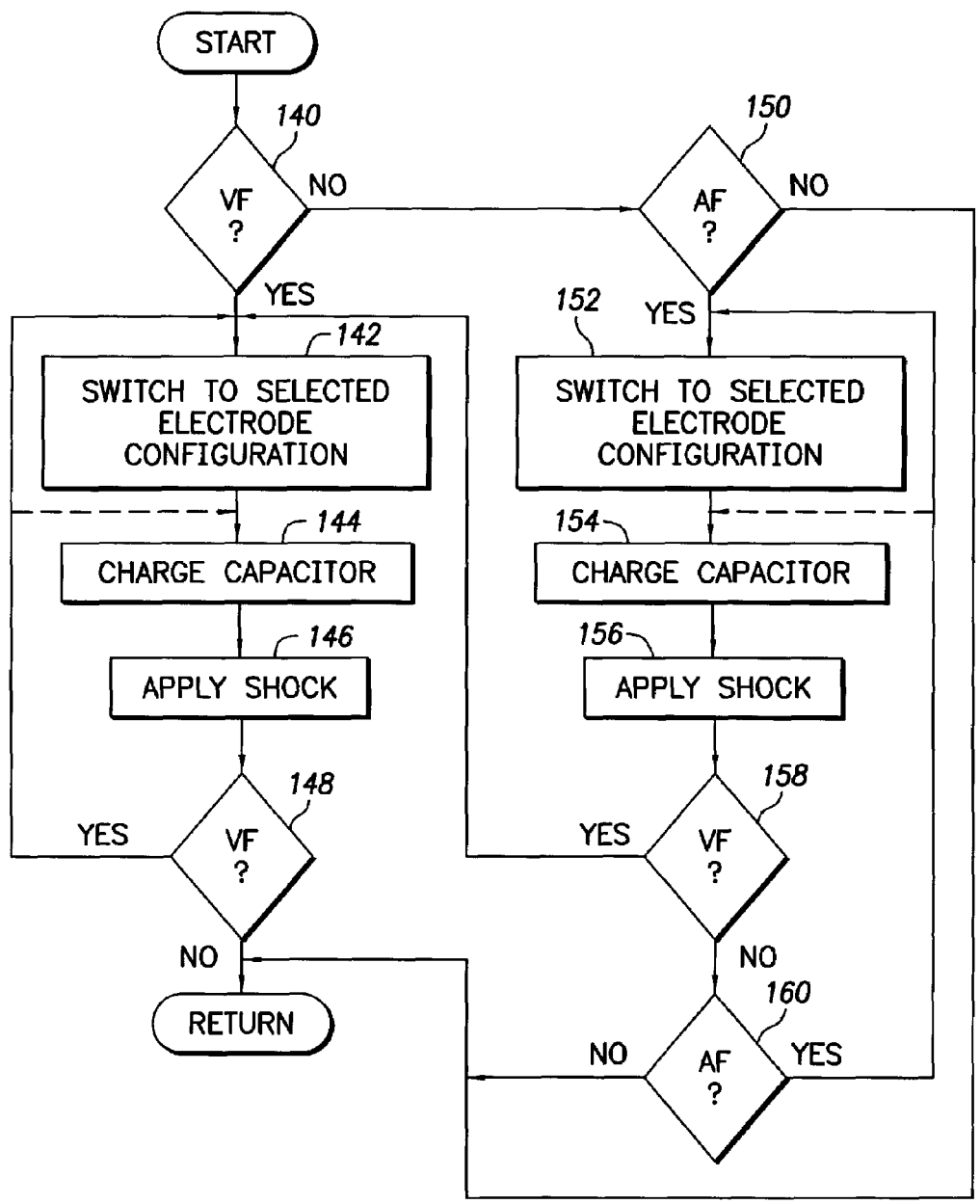
FIG. 2 is a flow chart describing a method of using the present invention to advantage.

FIG. 2, a flow chart describing a method of using the novel features of the present invention to advantage after the ventricular and atrial defibrillation electrode configurations to be used are selected. In this flow chart, and the other flow charts described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The method of FIG. 2 initiates at a decision block 140 wherein the arrhythmia detector 62 determines if ventricular fibrillation (VF) is present. If ventricular fibrillation is not detected by the arrhythmia detector 62, the method advances to a decision block 150 wherein the arrhythmia detector 62 determines if atrial fibrillation (AF) is present. If the heart 12 is not experiencing an episode of atrial fibrillation, the process returns, i.e., terminates. However, if the heart 12 is experiencing an episode of atrial fibrillation, the implantable stimulation device 10 proceeds to provide atrial defibrillation therapy in a manner to be described hereinafter.

Returning now to decision block 140, if it is determined in decision block 140 that the heart 12 is experiencing ventricular fibrillation, the process immediately advances to an activity step 142 wherein the selected ventricular defibrillation electrode configuration is selected by the microcontroller 60 and switch bank 74. For example, if the selected electrode configuration for ventricular defibrillation is the electrode configuration wherein the device case 40 is used as a cathode and the RV coil electrode 36 is used as an anode, the switch bank 74 will couple the shocking circuit output pair 131 to terminals 40 and 56 of the device. Following activity block 142, the method immediately advances to activity block 144 wherein the output capacitor of the shocking circuit 130 is charged to a preprogrammed ventricular defibrillation voltage level.

After the output capacitor is charged in accordance with activity block 144, the process then advances to step 146 wherein the ventricular defibrillation energy from the shocking circuit 130 is delivered through the switch bank 74 to the selected electrode configuration to defibrillate the ventricles. Once the defibrillating energy is applied to the ventricles, the method then advances to decision block 148 wherein it is determined if the ventricular fibrillation has been terminated. If the ventricular fibrillation has not been terminated, the process then returns to step 142 to once again initiate the ventricular fibrillation therapy. Alternatively, the method could return to step 144 if the switch bank 74 holds the selected electrode configuration in electrical connection with the shocking circuit outputs 131.

If, in decision block 148, it is determined that ventricular fibrillation is no longer present and hence has been terminated, the process returns, i.e., terminates. Decision block 140 will thereafter be repeated a preprogrammed time later to once again detect for ventricular fibrillation.

If, it is determined in decision block 140 that ventricular fibrillation is not present, the process advances to decision block 150 as previously described. If it is determined in decision block 150 that the heart 12 is experiencing an episode of atrial fibrillation, the method advances to activity block 152 wherein the microcontroller 60 and switch bank 74 selects and couples the selected atrial defibrillation electrode configuration to the outputs 133 of the shocking circuit 130. For example, the selected electrode configuration for atrial defibrillation may include the CS coil electrode 48 as an anode and the RA coil electrode 38 as a cathode. Once the switch bank 74 has selectively coupled the selected atrial defibrillation electrode configuration to outputs 133 of shocking circuit 130, the method advances to step 154 wherein the output capacitor for atrial defibrillation of the shocking circuit 130 is charged to a preprogrammed atrial defibrillation voltage level. When the capacitor is fully charged in accordance with activity block 154, the method proceeds to step 156 wherein the atrial defibrillation energy is applied from outputs 133, through the switch bank 74, and to the selected electrode configuration. Activity block 156 may further include a safety protocol for timing cardiac intervals and to ensure reliable R-wave detection. Preferably, the atrial defibrillation energy applied is synchronized to a first detected R-wave following a cardiac cycle having a cycle length greater than a minimum interval. This serves to minimize the probability of the atrial defibrillation shock inducing ventricular fibrillation.

Following activity block 156, the method advances to decision block 158 wherein the arrhythmia detector 62 determines if ventricular fibrillation is present. This step is implemented in the event that the atrial defibrillation shock induced ventricular fibrillation. If the heart 12 is determined in decision block 158 to be experiencing ventricular fibrillation, the method returns to step 142 to begin the process of delivering ventricular defibrillation therapy. However, if ventricular fibrillation is found to not be present in accordance with decision block 158, the method advances to step 160 wherein the arrhythmia detector 62 determines if the heart 12 is still experiencing an episode of atrial fibrillation. If atrial fibrillation is still present, the method then returns to step 152 to begin the process of delivering atrial defibrillation therapy. However, if in decision block 160 it is determined that the heart is no longer experiencing an episode of atrial fibrillation, and thus indicating that the atrial fibrillation has been terminated, the method then returns, i.e., terminates.

Alternatively, if in decision block 160, it is determined that atrial fibrillation is still present, the process could return to activity block 154. This would be advantageous if the selected atrial defibrillation electrode configuration is held in connection with the atrial defibrillation outputs until the atrial fibrillation is terminated.

As can be seen from the foregoing, the present invention provides an implantable cardiac stimulation system, device, and method wherein a plurality of electrode configurations are provided for both ventricular defibrillation and atrial defibrillation. At least one electrode configuration for ventricular defibrillation includes the device case to ensure effective ventricular fibrillation therapy. However, each of the electrode configurations of the atrial defibrillation electrode configurations is electrically isolated from the case and hence confined within the heart. This allows the selection of the best atrial defibrillation electrode configuration which exhibits the lowest atrial defibrillation threshold and/or which minimizes perception of discomfort to the patient from the atrial defibrillation shocks. Hence, the present invention affords effective ventricular defibrillation therapy while also providing effective atrial defibrillation therapy with minimized discomfort to the patient.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. An implantable cardiac stimulation system for selectively delivering arrhythmia termination pulses to at least one of a ventricle and an atrium of a patient's heart, the system comprising:
   an implantable cardiac stimulation device encapsulated in a conductive enclosure;
   a ventricular pulse generator and an atrial pulse generator disposed within the conductive enclosure, the ventricular pulse generator providing ventricular arrhythmia termination pulses and the atrial pulse generator providing atrial arrhythmia termination pulses;
   a first electrode configuration, including the conductive enclosure, arranged to be coupled to the ventricular pulse generator, to apply the ventricular arrhythmia termination pulses to the heart;
   wherein the first electrode configuration is one of a plurality of arrhythmia termination electrode configurations;
   a second electrode configuration, electrically independent from the conductive enclosure, arranged to be coupled to the atrial pulse generator, to apply the atrial arrhythmia termination pulses to the heart;
   wherein the second electrode is one of a plurality of arrhythmia termination electrode configurations;
   an electrode configuration selector to select one of the plurality of electrode configurations based upon an arrhythmia terminating characteristic; and
   wherein the arrhythmia terminating characteristic is based on minimizing atrial arrhythmia termination discomfort of the patient by confining each atrial arrhythmia termination electrode configuration of the plurality of arrhythmia termination electrode configurations to within the heart.

2. The system of claim 1 wherein the arrhythmia terminating characteristic is based upon ventricular defibrillation threshold.

3. The system of claim 1 wherein the atrial arrhythmia termination pulses are rounded to minimize pain to the patient.

4. The system of claim 1 wherein the arrhythmia termination characteristic is based upon atrial defibrillation threshold.

5. An implantable cardiac stimulation system for selectively delivering arrhythmia termination pulses to at least one of a ventricle and an atrium of a patient's heart, the system comprising:
   a pulse generator that provides arrhythmia termination pulses;
   a plurality of electrode configurations coupled to the pulse generator to apply atrial and ventricular arrhythmia termination pulses to the heart;
   at least one of the electrode configurations comprising first and second electrodes adapted for placement in different regions of the heart and coupled together to a cathode and a third electrode that defines an anode; and
   an electrode configuration selector to select one of the plurality of electrode configurations based upon an arrhythmia terminating characteristic;
   wherein circuitry is operative to deliver the arrhythmia termination pulses between the cathodal and anodal electrodes when the at least one electrode configuration is selected by the electrode configuration selector;
   wherein the plurality of electrode configurations further comprises:
   a first additional electrode configuration, including the conductive enclosure, arranged to be coupled to a ventricular pulse generator, to apply the ventricular arrhythmia termination pulses to the heart; and
   a second additional electrode configuration, electrically independent from the conductive enclosure, arranged to be coupled to an atrial pulse generator, to apply the atrial arrhythmia termination pulses to the heart;
   wherein the electrode configuration selector selects the second electrode configuration from among the plurality of atrial arrhythmia termination electrode configurations based upon an arrhythmia terminating characteristic; and
   wherein the arrhythmia terminating characteristic is based on minimizing atrial arrhythmia termination discomfort of the patient by confining each atrial arrhythmia termination electrode configuration of the plurality of electrode configurations to within the heart.

6. The system of claim 5 wherein the first electrode comprises an electrode in a right atrium, the second electrode comprises an electrode in a coronary sinus, and the third electrode comprises an electrode in a right ventricle.

7. The system of claim 5 wherein the arrhythmia terminating characteristic is based upon ventricular defibrillation threshold.

8. The system of claim 5 wherein the atrial arrhythmia termination pulses are rounded to minimize pain to the patient.

9. The system of claim 5 wherein the arrhythmia termination characteristic is based upon atrial defibrillation threshold.

10. A method for selectively delivering arrhythmia termination pulses to at least one of a ventricle and an atrium of a patient's heart, the method comprising:
    placing a plurality of electrode configurations in different regions of the heart, one of the placings comprising:
    placing first and second electrodes in different regions of the heart;
    coupling together the first and second electrodes to define an anode; and
    placing at least a third electrode in a region of the heart, wherein the third electrode defines a cathode;
    selecting the one of the plurality of electrode configurations based upon an arrhythmia terminating characteristic; and
    delivering one or more arrhythmia termination pulses between the cathodal and anodal electrodes when the one of the plurality of electrode configurations is selected; and
    detecting a ventricular arrhythmia of the heart;
    coupling a first additional electrode configuration to a pulse generator when a ventricular arrhythmia is detected, the first additional electrode configuration including a conductive housing to encapsulate an implantable cardiac stimulation device;
    triggering the pulse generator to provide a ventricular arrhythmia terminating pulse to the first additional electrode configuration;
    detecting an atrial arrhythmia of the heart;
    triggering the pulse generator to a second additional electrode configuration when an atrial arrhythmia is detected, the second additional electrode configuration being electrically independent from the conductive housing; and
    causing the pulse generator to provide an atrial arrhythmia terminating pulse to the second additional electrode configuration.

11. The method of claim 10 wherein the arrhythmia terminating characteristic is based upon ventricular defibrillation threshold.

12. The method of claim 10 wherein delivering one or more arrhythmia termination pulses comprises atrial arrhythmia termination pulses that are rounded to minimize pain to the patient.

13. The method of claim 10 wherein the arrhythmia termination characteristic is based upon atrial defibrillation threshold and a degree of perceived pain by the patient.

14. A method for selectively delivering arrhythmia termination pulses to at least one of a ventricle and an atrium of a patient's heart, the method comprising:
- detecting a ventricular arrhythmia of the heart;
- coupling a first electrode configuration to a pulse generator when a ventricular arrhythmia is detected, the first electrode configuration including a conductive housing to encapsulate an implantable cardiac stimulation device;
- wherein the first electrode configuration is one of a plurality of arrhythmia termination electrode configurations;
- triggering the pulse generator to provide a ventricular arrhythmia terminating pulse to the first electrode configuration;
- detecting an atrial arrhythmia of the heart;
- triggering the pulse generator to a second electrode configuration when an atrial arrhythmia is detected, the second electrode configuration being electrically independent from the conductive housing; and
- causing the pulse generator to provide an atrial arrhythmia terminating pulse to the second electrode configuration;
- wherein the second electrode configuration is one of a plurality of arrhythmia termination configurations for terminating an arrhythmia of the atria, and wherein each atrial arrhythmia terminating electrode configuration of the plurality of arrhythmia termination electrode configurations is configured to within the heart to minimize atrial arrhythmia termination discomfort of the patient.

15. The method of claim 14 wherein the arrhythmia terminating characteristic is based upon ventricular defibrillation threshold.

16. The method of claim 14 wherein delivering one or more arrhythmia termination pulses comprises atrial arrhythmia termination pulses that are rounded to minimize pain to the patient.

17. The method of claim 14 wherein the arrhythmia termination characteristic is based upon atrial defibrillation threshold and a degree of perceived pain by the patient.

* * * * *